US005710113A

United States Patent [19]
Wells

[11] Patent Number: 5,710,113
[45] Date of Patent: Jan. 20, 1998

[54] HAIR CONDITIONING COMPOSITIONS WITH SILICONE CONDITIONING AGENT CONTAINING SILICONE RESIN

[75] Inventor: Robert Lee Wells, Cincinnati, Ohio

[73] Assignee: The Procter & Gamble Company, Cincinnati, Ohio

[21] Appl. No.: 392,304

[22] Filed: Feb. 22, 1995

Related U.S. Application Data

[63] Continuation of Ser. No. 237,951, May 2, 1994, abandoned, which is a continuation of Ser. No. 64,724, May 9, 1993, abandoned, which is a continuation of Ser. No. 622,696, Dec. 5, 1990, abandoned.

[51] Int. Cl.$^6$ ............................... C11D 1/82; C11D 1/76; C11D 1/12
[52] U.S. Cl. .................. 510/122; 510/466; 510/127; 510/493; 510/426
[58] Field of Search ...................... 252/174.15, 547, 252/550, DIG. 13, DIG. 2; 510/122, 466, 127, 493, 426

[56] References Cited

U.S. PATENT DOCUMENTS

| | | | |
|---|---|---|---|
| 2,826,551 | 3/1958 | Geen | 252/89 |
| 3,964,500 | 6/1976 | Drakoff | 132/7 |
| 4,364,837 | 12/1982 | Pader | 252/173 |
| 4,597,962 | 7/1986 | Grollier et al. | 429/47 |
| 4,673,568 | 6/1987 | Grollier et al. | 424/47 |
| 4,704,272 | 11/1987 | Oh et al. | 424/70 |
| 4,710,314 | 12/1987 | Madrange et al. | 252/117 |
| 4,726,944 | 2/1988 | Osipow et al. | 424/70 |
| 4,728,457 | 3/1988 | Fieler et al. | 252/174.15 |
| 4,741,855 | 5/1988 | Grote et al. | 252/142 |
| 4,788,006 | 11/1988 | Bolich, Jr. et al. | 252/550 |
| 4,820,308 | 4/1989 | Madrange et al. | 8/405 |
| 4,842,850 | 6/1989 | Vu | 424/70 |
| 4,902,499 | 2/1990 | Bolich, Jr. et al. | 424/70 |
| 4,906,459 | 3/1990 | Cobb et al. | 424/70 |
| 4,983,383 | 1/1991 | Maksimoski et al. | 424/70 |
| 5,085,857 | 2/1992 | Reid et al. | 424/70 |
| 5,277,899 | 1/1994 | McCall | 424/71 |

FOREIGN PATENT DOCUMENTS

| | | |
|---|---|---|
| 56-72095 | 6/1981 | Japan . |
| 2042008 | 2/1990 | Japan . |
| 2188518 | 7/1990 | Japan . |
| 2188519 | 7/1990 | Japan . |
| 849433 | 9/1960 | United Kingdom . |

OTHER PUBLICATIONS

Hardman and Torkelson, General Electric Co., "Silicones", reprinted from Ency. of Polymer Science & Engineering, vol. 15, 2nd Ed., 1989, J. Wiley & Sons, Inc., pp. 265–270.

*Primary Examiner*—Paul Lieberman
*Assistant Examiner*—Charles Boyer
*Attorney, Agent, or Firm*—David K. Dabbiere; Leonard W. Lewis; David L. Suter

[57] ABSTRACT

Disclosed are hair conditioning compositions, including hair rinse and shampoo compositions, containing a silicone fluid hair conditioning compoentn with improved efficiency through the use of silicone resins, wherein the weight ratio of the silicone fluid component to silicone resin is from about 4:1 to about 400:1.

28 Claims, No Drawings

HAIR CONDITIONING COMPOSITIONS WITH SILICONE CONDITIONING AGENT CONTAINING SILICONE RESIN

This is a continuation of application Ser. No. 08/237,951, filed on May 2, 1994 now abandoned, which is a continuation of application Ser. No. 08/064,724, filed on May 19, 1993, now abandoned, which is a continuation of application Ser. No. 07/622,696, filed on Dec. 5, 1990 now abandoned.

TECHNICAL FIELD

The present invention is related to hair conditioning compositions having dispersed, non-volatile silicone conditioning agents, including hair rinse compositions and hair-conditioning shampoo compositions.

BACKGROUND OF THE INVENTION

Human hair becomes soiled due to its contact with the surrounding atmosphere and, to a greater extent, from sebum secreted by the head. The build-up of sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair can be left in a wet, tangled and generally unmanageable state. Shampooing can also result in the hair becoming dry or "frizzy" due to the removal of natural oils or other hair moisturizing materials. After shampooing, the hair can also suffer from a perceived loss of "softness". Softness, of course, is a generally desirable attribute for many users of shampoo products. A variety of approaches have been developed to alleviate the after-shampoo problems. These range from the inclusion of hair conditioning aids in shampoos to post-shampoo application of hair conditioners, i.e., hair rinses. Hair rinses typically work by depositing a polymeric film, cationic hair conditioning surfactant, or other material onto the hair. However, such solutions to a very prevalent problem have not been fully satisfactory. For one thing, hair rinses are generally liquid in nature and must be applied in a separate step following the shampooing, left on the hair for a length of time, and rinsed with fresh water. This, of course, is time consuming and is not convenient.

While shampoos have been disclosed which contain conditioning aids, they have not been totally satisfactory for a variety of reasons. A prevalent problem relates to compatibility problems between good cleaning anionic surfactants and the conventional cationic agents which are good conditioning agents.

Silicones are materials which can provide excellent hair conditioning benefits and which are not incompatible with anionic detersive surfactants.

Silicones in shampoo compositions have been disclosed in a number of different publications. Such publications include U.S. Pat. No. 2,826,551, Geen, issued Mar. 11, 1958; U.S. Pat. No. 3,964,500, Drakoff, issued Jun. 22, 1976; U.S. Pat. 4,364,837, Pader, issued Dec. 21, 1982; and British Patent 849,433, Woolston, issued Sep. 28, 1960. While these patents disclose silicone containing compositions, they did not provide answers to all of the problems encountered in making a satisfactory product. One problem is that of keeping a dispersed, insoluble silicone material suspended and the total product stable. Recently, stable silicone-containing hair conditioning shampoos have been described in U.S. Pat. No. 4,741,855, Grote and Russell, issued May 3, 1988, which discloses shampoo with cleaning surfactant, an insoluble, non-volatile silicone, water, and a suspending agent such as long chain esters of ethylene glycol, esters of long chain fatty acids, long chain amine oxides, etc. Stable silicone-containing hair conditioning shampoos have also been disclosed in U.S. Pat. No. 4,788,066, Bolich and Williams, issued Nov. 29, 1988, which discloses a xanthan gum suspending agent.

Stable, silicone-containing hair conditioning shampoos have recently attained substantial success in the marketplace. Whereas these shampoos can provide excellent hair conditioning benefits to the user, it would nevertheless be desirable to improve these types of shampoos by increasing the efficiency of the silicone hair conditioner incorporated into such shampoo in order to reduce the amount of silicone that is incorporated into the shampoo and, consequently, to reduce raw materials cost. One factor affecting effectiveness of the silicone hair conditioner is the ability of the silicone to deposit upon the hair.

Thus it is an object of this invention to provide silicone hair conditioning compositions that have improved ability to deposit upon the hair.

It is another object of this invention to specifically provide silicone hair conditioner-containing shampoo compositions characterized by improved silicone hair conditioner deposition upon the hair.

These and other objects will become apparent from the Summary of the Invention and Detailed Description of the Invention which follow.

Unless otherwise indicated, all percentages are calculated by weight of the total composition and all ratios are calculated on a weight basis.

SUMMARY OF THE INVENTION

The present invention provides silicone hair conditioning compositions having improved silicone hair conditioner deposition upon the hair. These compositions include hair-conditioning shampoos as well as other hair conditioning compositions such as hair rinse compositions which are typically applied to wet or damp hair after shampoo is applied and rinsed off. The compositions of the present invention have a hair conditioning component dispersed in said compositions, wherein the hair conditioning component comprises a combination of a nonvolatile, insoluble silicone fluid component, as a hair conditioning agent, and a low level of silicone resin which is soluble in the silicone fluid.

The hair conditioning compositions hereof also include one or more carriers, typically including water, and for liquid compositions preferably a suspending agent for maintaining the silicone-containing hair conditioning component suspended in the composition. The shampoo compositions hereof are further characterized by the presence of one or more detersive, or "cleaning", surfactants. It has been found that the silicone resin, when present at low levels as set forth herein, can increase the level of deposition of the silicone fluid upon the hair. In particular, the weight ratio of silicone fluid: silicone resin should be from about 4:1 to about 400:1, preferably from about 9:1 to about 200:1, more preferably from about 19:1 to about 100:1.

In a particular embodiment, the present invention provides a hair conditioning composition useful for rinse-off hair treatment comprising:

(a) from about 0.1% to about 10%, by weight, of a dispersed, silicone hair conditioning component, said hair conditioning component comprising a combination of:

(i) nonvolatile silicone fluid component which is insoluble in water and in said hair conditioning composition; and (ii) silicone resin, said silicone resin being soluble in said silicone fluid and insoluble in water and in said hair conditioning composition;

wherein the weight ratio of (i):(ii) is from about 4:1 to about 400:1, preferably from about 9:1 to about 200:1, more preferably from about 19:1 to about 100:1; and
(b) a liquid carrier.

In a specific hair conditioning embodiment, the present invention provides a shampoo composition comprising:
(a) from about 5% to about 50% of a detersive surfactant component;
(b) from about 0.1% to about 10% of a dispersed, silicone hair conditioning component, said hair conditioning component comprising a combination of:

(i) a nonvolatile silicone fluid component which is insoluble in water and in said hair conditioning composition; and (ii) silicone resin which is soluble in said silicone fluid and insoluble in water and in said shampoo composition;

wherein the weight ratio of (i):(ii) is from about 4:1 to about 400:1, preferably from about 9:1 to about 200:1, more preferably from about 19:1 to about 100:1; and
(c) a liquid carrier.

The invention, including preferred embodiments thereof, is described in more detail in the Detailed Description of the Invention, which follows.

DETAILED DESCRIPTION OF THE INVENTION

The essential as well as certain preferred and optimal components of the compositions of the present invention are described below.

Silicone Hair Conditioning Component

The silicone hair conditioning component comprises a mixture of a nonvolatile silicone fluid component, comprising one or more silicone fluids and optionally comprising one or more silicone gums, as a hair conditioning agent, and a silicone resin component, comprising one or more silicone resins. The resin must be soluble in the silicone fluid and should also be insoluble in both water and the hair conditioning composition.

The mixture of silicone fluid component and resin is dispersed in the hair conditioning compositions in the form of droplets. Without intending to be limited to anything, it is believed that the silicone resin migrates toward the periphery of the droplets and thereby induces spreading of the silicone fluid upon deposit on the hair. The resulting increased area of contact between silicone fluid and hair is believed to facilitate enhanced deposition.

The silicone resin is used at low levels relative to the silicone fluid. In particular, the weight ratio of silicone fluid to silicone resin should be from about 4:1 to about 400:1, preferably from about 9:1 to about 200:1, more preferably from about 19:1 to about 100:1. The hair conditioning compositions hereof will generally comprise from about 0.1% to about 10%, by weight, of the silicone hair conditioning component, typically from about 0.5% to about 8%. Shampoo compositions, in particular, will generally comprise from about 0.1% to about 10%, by weight, of the silicone hair conditioning component, typically from about 0.5% to about 8%, preferably from about 1% to about 5%. Hair rinse compositions will also generally comprise from about 0.1% to about 10%, by weight, of the silicone hair conditioning component, typically from about 0.3% to about 8%, preferably from about 0.5% to about 5%. Silicone fluid and silicone resins that can be used are described in more detail below.

Silicone Fluid Component

An essential component of the present invention is a nonvolatile, nonionic silicone conditioning component which is insoluble in the shampoo compositions hereof. The silicone conditioning component comprises a nonvolatile, insoluble silicone fluid and optionally comprises a silicone gum which is insoluble in the shampoo composition as a whole but is soluble in the. silicone fluid. The silicone conditioning agent for use herein in shampoo compositions will preferably have viscosity of from about 1,000 to about 2,000,000 centistokes at 25° C., more preferably from about 10,000 to about 1,800,000 centistokes, even more preferably from about 100,000 to about 1,500,000 centistokes. Lower viscosity nonvolatile silicone fluids, however, can also be used and may be desirable particularly in the case of hair rinse compositions. Volatile silicone fluids, typically having viscosity less than 5 centistokes at 25° C., may also be utilized in hair rinse compositions. The level of volatile silicones in shampoo compositions, however, is preferably at levels of less than about 0.5% by weight of the total composition. The viscosity can be measured by means of a glass capillary viscometer as set forth in Dow Corning Corporate Test Method CTM0004, Jul. 20, 1970.

Suitable nonvolatile silicone fluids for use in hair conditioning agents include polyalkyl siloxanes, polyaryl siloxanes, polyalkylaryl siloxanes, polyether siloxane copolymer and mixtures thereof. However, any silicone fluid having hair conditioning properties may be used. As used hereinafter, the term "insoluble" in reference to silicone fluid or silicone resin shall mean that the silicone material is not soluble in either water or in the hair conditioning composition. The term "nonvolatile" in reference to the silicone fluid as used herein shall be interpreted according to the meaning well understood to those skilled in the art, i.e., the silicone fluid exhibits very low or no significant vapor pressure at ambient conditions. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000 centistokes. The term "silicone", as used herein, shall be synonomous with the term "polysiloxane".

The nonvolatile polyalkyl siloxane fluids that may be used include, for example, polydimethylsiloxanes. These siloxanes are available, for example, from the General Electric Company as a Viscasil series and from Dow Corning as the Dow Corning 200 series. Preferably, the viscosity ranges from about 10 centistokes to about 100,000 centistokes at 25° C.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymer that may be used includes, for example, a polypropylene oxide modified dimethylpolysiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Silicone fluids hereof also include polyalkyl or polyaryl siloxanes with the following structure:

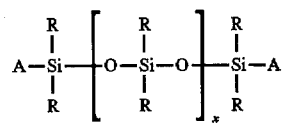

wherein R is alkyl or aryl, and x is an integer from about 7 to about 8,000 may be used. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporated herein by reference is *Silicon Compounds* distributed by Petrarch Systems, Inc., 1984. This reference provides an extensive (though not exclusive) listing of suitable silicone fluids.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, *Chemistry and Technology of Silicones*, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane fluid having a viscosity of from about 10 centipoise to about 100,000 centistokes, wherein the ratio of gum to fluid is from about 30:70 to about 70:30, preferably from about 40:60 to about 60:40.

Cationic silicone fluids and gums may be used although the nonionic silicone fluids and gums are preferred.

Silicone Resin

The other essential component of the silicone hair conditioning component is silicone resin. Silicone resins are highly crosslinked polymeric siloxane systems. The crosslinking is introduced through the incorporation of trifunctional and tetrafunctional silanes with monofunctional or difunctional, or both, monomer units during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone resins will generally have at least about 1.1 oxygen atoms per silicon atom. Preferably, the ratio of oxygen:silicon atoms is at least about 1.2:1.0. Typical silanes used in the manufacture of silicone resins are monomethyl-, dimethyl-, monophenyl-, diphenyl-, methylphenyl-, monovinyl-, and methylvinyl-chlorosilanes, and tetrachlorosilane. Preferred resins are the methyl substituted silicone resins, such as those offered by General Electric as GE SS4230 and SS4267. Commercially available silicone resins will generally be supplied in an unhardened form in a low viscosity volatile or nonvolatile silicone fluid. The silicone resins for use herein should be supplied and incorporated into the present compositions in such non-hardened form rather than as a hardened resin, as will be readily apparent to those skilled in the art.

Background material on silicones including sections discussing silicone fluids, gums, and resins, as well as manufacture of silicones, can be found in *Encyclopedia of Polymer Science and Engineering*, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetrafunctional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q molar ratio is from about 0.5:1.0 to about 1.5:1.0 and the average molecular weight of the resin is from about 1000 to about 10,000.

The weight ratio of the nonvolatile silicone fluid component to the silicone resin component is from about 4:1 to about 400:1. Preferably such ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above.

Aqueous Carrier

An aqueous carrier is the last essential component of the present invention, except for shampoo compositions which also must contain detersive surfactants. It is generally present at a level of from about 20% to about 95%, preferably from about 60% to about 85%, for pourable, liquid formulations. The compositions of the present invention can also be in other forms, such as gels, mousse, etc. In such cases, appropriate components known in the art such as gelling agents (e.g., hydroxyethyl cellulose), etc. can be included in the compositions. Gels will typically contain from about 20% to about 90% water. Mousses will contain aerosol propellant in a low viscosity composition and are packaged in an aerosol can, according to techniques well known in the art.

Suspending Agent

Any suspending agent useful for suspending the silicone hair conditioning component in dispersed form in the hair conditioning compositions hereof can be used. A suspending agent is particularly important in pourable liquid formulations. They can also be used in gel formulations to suspend the silicone, water, and other ingredients of the composition.

The suspending agents useful in the present compositions include any of several long chain acyl derivative materials or mixtures of such materials, such as long chain acyl derivatives, long chain amine oxides, and mixtures thereof, wherein such suspending agents are present in the composition in crystalline form. These suspending agents are described in U.S. Pat. No. 4,741,855, Grote and Russell, issued May 3, 1988, incorporated herein by reference. Included are ethylene glycol esters of fatty acids having from about 16 to about 22 carbon atoms. Preferred are the ethylene glycol stearates, both mono and distearate, but particularly the distearate containing less than about 7% of the mono stearate. Other suspending agents found useful are alkanol amides of fatty acids, having from about 16 to about 22 carbon atoms, preferably about 16 to 18 carbon atoms. Preferred alkanol amides are stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmirate, etc.); glyceryl esters (e.g., glyceryl distearate) and long chain esters of long chain alkanol amides (e.g., stearamide DEA distearate, stearamide MEA stearate).

Still other suitable suspending agents are alkyl ($C_{16}$–$C_{22}$) dimethyl amine oxides such as stearyl dimethyl amine oxide. If the compositions contain an amine oxide or a long chain acyl derivative as a surfactant the suspending function could also be provided by such surfactant and additional suspending agent may not be needed if the level of those materials are at least the minimum level given below.

Other long chain acyl derivatives that can be used include N,N-dihydrocarbyl amido benzoic acid and soluble salts thereof (e.g., Na and K salts), particularly N,N-di (hydrogenated) $C_{16}$, $C_{18}$ and tallow amido benzoic acid species of this family, which are commercially available from Stepan Company (Northfield, Ill., USA).

The long chain acyl derivative materials, when utilized as the suspending agent, are typically present in pourable, liquid formulations at a level of from about 0.1% to about 5.0%, preferably from about 0.5% to about 3.0%. The suspending agent serves to assist in suspending the silicone material and may give pearlescence to the product. Mixtures of suspending agents are also suitable for use in the compositions of this invention.

Another type of suspending agent that can be used is xanthan gum. Shampoo compositions utilizing xanthan gum as a suspending agent for the silicone hair conditioning component are described in U.S. Pat. No. 4,788,006, Bolich and Williams, issued Nov. 29, 1988, incorporated herein by reference. Xanthan gum is biosynthetic gum material that is commercially available. It is a heteropolysaccharide with a molecular weight of greater than 1 million. It is believed to contain D-glucose, D-mannose and D-glucuronate in the molar ratio of 2.8:2.0:2.0. the polysaccharide is partially acetylated with 4.7% acetyl. This information and other is found in Whistler, Roy L. Editor *Industrial Gums—Polysaccharides and Their Derivatives* New York: Academic Press, 1973. Kelco, a Division of Merck & Co., Inc. offers xanthan gum as Keltrol®. The gum, when used as the silicone hair conditioning component suspending agent, will typically be present in pourable, liquid formulations at a level of from about 0.3% to about 3%, preferably from about 0.4% to about 1.2% in the compositions of the present invention.

Combinations of long chain acyl derivatives and xanthan gum are disclosed as a suspending agent for silicone hair conditioners in U.S. Pat. No. 4,704,272, Oh et al., issued Nov. 3, 1987, incorporated herein by reference, and may also be used in the present compositions. Gel formulations have high levels of suspending agent relative to pourable, liquid formulations when used as the primary means of imparting the gel-like viscosity to the composition. In such compositions, the suspending agent will typically be present at levels of from about 0.1 to about 5%. Alternately, other materials can be used to impart a gel-like viscosity to the composition, such as gelling agents (e.g., hydroxyethyl cellulose), thickeners, viscosity modifiers, etc. Mixtures of these materials can also be used.

Detersive Surfactant

The hair conditioning compositions of the present invention can comprise a detersive surfactant to provide cleaning performance to the composition. Shampoo compositions will, of course, include detersive surfactant as an essential element. Whereas, as set forth in the background to the invention, a primary commercial application of silicone hair conditioners can be found in the context of shampoo compositions, it will be understood by those skilled in the art upon reading this document that the benefits of the improved silicone hair conditioning component obtained by incorporating a silicone resin into the hair conditioner as described above can be obtained in hair conditioning compositions not containing detersive surfactant ingredients, such as hair rinse compositions applied subsequent to shampooing.

The detersive surfactant, when utilized as a cleaning ingredient, particularly in shampoo compositions, will generally be from about 5% to about 50%, preferably from about 8% to about 30%, more preferably from about 10% to about 25%, of the composition. A wide variety of surfactant materials may be utilized including anionic, nonionic, cationic, zwitterionic and amphoteric surfactants. Cationic detersive surfactants, if used, should not significantly interfere with the effectiveness of anionic surfactants included for detersive purposes. As discussed previously, it is a particular benefit of silicone conditioning agent technology that anionic detersive surfactants can be used without adverse interaction between surfactant and conditioning agent. Synthetic anionic detergents useful herein include alkyl and alkyl ether sulfates. These materials have the respective formulae $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having from about 8 to about 24 carbon atoms. Preferably, R has from about 12 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and/or ammonium salts of coconut alkyl triethylene glycol ether sulfate, tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. Such a mixture also comprises from about 0 to about 20% by weight $C_{12-13}$ compounds; from about 60 to about 100% by weight of $C_{14-15-16}$ compounds, from about 0 to about 20% by weight of $C_{17-18-19}$ compounds; from about 3 to about 30% by weight of compounds having a degree of ethoxylation of 0; from about 45 to about 90% by weight of compounds having a degree of ethoxylation of from about 1 to about 4; from about 10 to about 25% by weight of compounds having a degree of ethoxylation of from about 4 to about 8; and from about 0.1 to about 15% by weight of compounds having a degree of ethoxylation greater than about 8.

Another suitable class of anionic surfactants are the water-soluble salts of the organic, sulfuric acid reaction products of the general formula:

$$R_1-SO_3-M$$

wherein $R_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Additional examples of anionic synthetic surfactants which come within the terms of the present invention are the reaction products of fatty acids esterified with isethionic acid and neutralized with sodium hydroxide where; for example, the fatty acids are derived from coconut oil; sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278.

Still other anionic synthetic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of $\alpha$-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The $\alpha$-olefins from which the olefin sulfonates are derived are mono-olefins having about 12 to about 24 carbon atoms, preferably about 14 to about 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific $\alpha$-olefin sulfonate mixture of the above type is described more fully in the U.S. Pat. No. 3,332,880, Pflaumer and Kessler, issued Jul. 25, 1961, incorporated herein by reference.

Another class of anionic organic surfactants are the $\beta$-alkyloxy alkane sulfonates. These compounds have the following formula:

$$R_1-\overset{\overset{\displaystyle OR_2}{|}}{\underset{\underset{\displaystyle H}{|}}{C}}-\overset{\overset{\displaystyle H}{|}}{\underset{\underset{\displaystyle H}{|}}{C}}-SO_3M$$

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Specific examples of $\beta$-alkyloxy-alkane-1-sulfonates, or alternatively 2-alkyloxy-alkane-1-sulfonates, having low hardness (calcium ion) sensitivity useful herein include: potassium-$\beta$-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecyl-sulfonate, sodium $\beta$-methoxyoctadecylsulfonate, and ammonium $\beta$-n-propoxydodecylsulfonate.

Many additional synthetic anionic surfactants are described in McCutcheon's Emulsifiers and Detergents, 1989 Annual, published by M. C. Publishing Co., which is incorporated herein by reference. Also U.S. Pat. No. 3,929,678, Laughlin et al., issued Dec. 30, 1975, discloses many other anionic as well as other surfactant types and is incorporated herein by reference.

Nonionic surfactants, which can be used, preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to about 20 carbon atoms, preferably from about 6 to about 12, in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

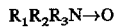

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyl-octylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

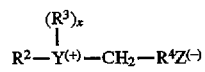

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxy-propane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl) ammonio]-butane-1 -carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Other zwitterionics such as betaines can also be useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amido-betaines and amidosulfobetaines, wherein the $RCONH(CH_2)_3$ radical is attached to the nitrogen atom of the betaine are also useful in this invention. Preferred betaines for use in the present compositions are cocoamidopropyl betaine, cocobetaine, lauryl amidopropyl betaine, and oleyl betaine.

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528.378.

Cationic detersive surfactants can also be used, although the use of anionic, nonionic, amphoteric, and zwitterionic surfactants is preferred. Cationic detersive surfactants are well known in the art. Generally, the cationic detersive surfactants will be quaternary ammonium compounds or amino compounds that are positively charged when dissolved in the compositions hereof as well as at neutral pH.

The above-mentioned surfactants can be used alone or in combination in the hair care compositions of the present invention. Preferred surfactants for use in the present shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl safcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, cocoamidopropyl betaine, cocobetaine, lauryl amido propyl betaine, oleyl betaine, and cocoamphocarboxyglycinate.

The most preferred shampoos of the present invention contain specific combinations of anionic surfactants, zwitterionic surfactants, and amphoteric surfactants. The preferred shampoos contain from about 2% to about 16% of alkyl sulfates and from 0% to about 14% of ethoxylated alkyl sulfates with a total surfactant level of from about 15% to about 20%.

Optional Components

The compositions herein can contain a variety of non-essential optional components. Such optional ingredients include, for example, preservatives such as benzyl alcohol, methyl paraben, propyl paraben and imidazolidinyl urea; cationic conditioning agents, including both cationic conditioning surfactants and cationic conditioning polymers; thickeners and viscosity modifiers such as a diethanolamide of a long chain fatty acid (e.g., PEG 3 lauramide), block polymers of ethylene oxide and propylene oxide such as Pluronic F88 offered by BASF Wyandotte, sodium chloride, sodium sulfate, ammonium zylene sulfonate, propylene glycol, polyvinyl alcohol, and ethyl alcohol; gelling agents such as hydroxyethyl cellulose; pH adjusting agents such as citric acid, succinic acid, phosphoric acid, sodium hydroxide, sodium carbonate, etc.; perfumes; dyes; and sequestering agents such as disodium ethylenediamine tetraacetate. This list of optional ingredients is not meant to be exclusive, and other optional components can be utilized.

These optional ingredients generally are used individually at a level of from about 0.01% to about 10%, most commonly from about 0.5% to about 5.0% by weight of the composition.

A variety of cationic surfactants useful as detersive surfactants and as conditioning agents are well known in the art. These materials contain amino or quaternary ammonium hydrophilic moieties which are positively charged when dissolved in the aqueous composition of the present invention. Whether the cationic surfactant functions as a detersive surfactant or a conditioning agent, or both, will depend upon the particular compound as is well understood by those skilled in the art. In general, compounds with longer chain length moieties attached to the cationic nitrogen tend to exhibit greater conditioning benefits. Cationic surfactants among those useful herein are disclosed in the following documents, all incorporated by reference herein: M.C. Publishing Co., *McCutcheon's, Detergents & emulsifiers*, (North American edition 1989); Schwartz et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Quaternary ammonium salts include dialkyldimethyl-ammonium chlorides and trialkyl methyl ammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). These types of cationic surfactants are useful as hair conditioning agents. Examples of quaternary ammonium salts useful herein include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride and tricetyl methyl ammonium chloride are particularly preferred quaternary ammonium salts. Preferred of the conventional cationic conditioning agents are cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; These materials may also provide anti-static benefits to the present shampoo compositions.

Salts of primary, secondary and tertiary fatty amines are also suitable cationic surfactant materials. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearyl amine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

Cationic conditioning surfactants especially useful in shampoo formulations are quaternary ammonium or amino compounds having at least one N-radical containing one or more nonionic hydrophilic moieties selected from alkoxy, polyoxyalkylene, alkylamido, hydroxyalkyl, and alkylester moieties, and combinations thereof. The surfactant contains at least one hydrophilic moiety within 4, preferably within 3, carbon atoms (inclusive) of the quaternary nitrogen or cationic amino nitrogen. For purposes herein, this means that the closest non-carbon atom in the hydropholic moiety to the cationic nitrogen must be within the stated number of carbon atoms relative to said nitrogen. Additionally, carbon atoms that are part of a hydrophilic moiety, e.g., carbon atoms carbon atoms in a hydrophilic polyoxyalkylene (e.g., —$CH_2$—$CH_2$—O—), that are adjacent to other hydrophilic moieties are not counted when determining the number of hydrophilic moieties within 4, or preferably 3, carbon atoms of the cationic nitrogen. In general, the alkyl portion of any hydrophilic moiety is preferably a $C_1$–$C_3$ alkyl. Suitable hydrophile-containing radicals include, for example, ethoxy, propoxy, polyoxyethylene, polyoxypropylene, ethylamido, propylamido, hydroxymethyl, hydroxyethyl, hydroxypropyl, methylester, ethylester, propylester, or mixtures thereof, as nonionic hydrophile moieties. The amino surfactants must be positively charged at the pH of the shampoo compositions. Generally, the pH of the shampoo compositions will be less than about 10, typically from about 3 to about 9.

Among the quaternary ammonium cationic surfactants useful herein are those of the general formula:

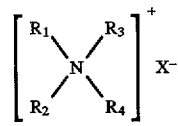

wherein $R_1$, $R_2$, $R_3$ and $R_4$ radicals comprise, independently, substituted or unsubstituted hydrocarbyl chains of from 1 to about 30 carbon atoms, or a hydrocarbyl having from 1 to about 30 carbon atoms and containing one or more aromatic, ether, ester, amido, or amino moieties present as substituents or as linkages in the radical chain, wherein at least one of the $R_1$–$R_4$ radicals contains one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof. Preferably, the cationic conditioning surfactant contains from 2 to about 10 nonionic hydrophile moieties located within the above stated ranges. For purposes herein, each hydrophilic amido, alkoxy, hydroxyalkyl, alkylester, alkylamido or other unit is considered to be a distinct nonionic hydrophile moiety. X is a soluble salt forming anion preferably selected from halogen (especially chlorine), acetate, phosphate, nitrate, sulfonate, and alkyl sulfate radicals.

Preferred quaternary ammonium salts include polyoxyethylene (2) stearyl methyl ammonium chloride, methyl bis (hydrogenated tallowamidoethyl) 2-hydroxyethyl ammonium methyl sulfate, polyoxypropylene (9) diethyl methyl ammonium chloride, tripolyoxyethylene (total PEG:10) stearyl ammonium phosphate, bis(N-hydroxyethyl-2-oleyl imidazolinium chloride) polyethylene glycol (12), and isododecylbenzyl triethanolammonium chloride.

Other ammonium quaternary and amino surfactants include those of the above general formula in the form of ring structures formed by covalently linking two of the radicals. Examples of such cationic surfactants include imidazolines, imidazoliniums, and pyridiniums, etc., wherein said surfactant has at least one nonionic hydrophile-containing radical as set forth above. Specific examples include 2-heptadecyl-4,5-dihydro-1H-imidazol-1-ethanol, 4,5-dihydro-1-(2-hydroxyethyl)-2-isoheptadecyl-1-phenylmethylimidazolium chloride, and 1-[2-oxo-2-[[2-[(1-oxooctadecyl)oxy]ethyl]amino]ethyl] pyridinium chloride.

Salts of primary, secondary and tertiary fatty amines are also preferred cationic surfactant materials. The alkyl groups of such amines preferably have from about 1 to about 30 carbon atoms and must contain at least one, preferably 2 to about 10, nonionic hydrophilic moieties selected from alkoxy, polyoxyalkylene, alkylamido, hydroxyalkyl, and alkylester moieties, and mixtures thereof. Secondary and tertiary amines are preferred, tertiary amines are particularly preferred. Specific examples of suitable amines include diethyl aminoethyl polyoxyethylene (5) laurate, cocopolyglyceryl-4 hydroxypropyl dihydroxy ethylamine, and dihydroxyethyl tallowamine hydrochloride.

Another type of cationic hair conditioning agent that can be advantageously incorporated into the compositions hereof especially into shampoos, encompasses quaternary ammonium and cationic amino polymeric conditioning agents. Such materials are known in the art, and a variety of such materials can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982). Especially useful among these are organic polymers characterized by open chain backbone, with quaternary ammonium or cationic amino moieties, or a mixture thereof, and a charge density which is no greater than about +3.0 meq/gram. Preferably, charge density is less than about +2.75 meq/gram. The precise cationic charge density is not believed to be critical as long as it is less than those stated essential and preferred limits. However, for practical reasons, the charge density should be of a level such that efficient substantivity between the polymer and the hair can be attained. Generally, it is preferred that cationic charge density be at least about 0.2 meq/gram, more preferably at least about 0.4 meq/gram. Generally, the shampoo pH will be between about 3 and about 9, preferably between about 4 and about 8. Those skilled in the art will recognize that the charge density of amino-containing polymers may vary depending upon pH and the isoelectric point of the amino groups. Additionally, it is preferred that the charge density be within the above limits at the pH of intended use which will, in general, be from about pH 4 to about pH 9, most generally from about pH 5 to about pH 8. The polymer, of course, must remain cationic upon application to the hair in order for there to be adequate substantivity between the conditioning agent and the hair.

Suitable cationic polymers include, for example, copolymers of vinyl monomers having cationic amine or quaternary ammonium functionalities with water soluble spacer monomers such as acylamide, methacrylamide, alkyl and dialkyl acrylamides, alkyl and dialkyl methacrylamides, alkyl acrylate, alkyl methacrylate, vinyl caprolactone, and N-vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

Tertiary amine-substituted vinyl monomers can be polymerized in the amine form, or can be converted to ammonium by a quaternization reaction. The amines can also be similarly quaternized subsequent to formation of the polymer.

Tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium. X can be, for example, a halide (e.g., Cl, Br, I, or F, preferably Cl, Br, or I) or a sulfate.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, vinyl quaternary ammonium monomers having cyclic cationic nitrogen-containing rings such as pyridinium and imidazolium, e.g., alkyl vinyl imidazolium and alkyl vinyl pyridinium salts. The alkyl portions of these monomers are preferably lower alkyls such as the $C_1$–$C_3$ alkyls, more preferably $C_1$ and $C_2$ alkyls. The quaternary ammonium salts must, of course, be soluble, and the anionic counterions referred to above are suitable.

The amine-substituted monomers useful for cationic organic polymers hereof will preferably be secondary or tertiary amines, more preferably tertiary amines. Suitable amine-substituted vinyl monomers for use herein include dialkylaminoalkyl acrylate, dialkylaminoalkyl methacrylate, dialkylaminoalkyl acrylamide, dialkylaminoalkyl and methacrylamide wherein the alkyl groups are preferably $C_1$–$C_7$, more preferably $C_1$–$C_3$, alkyls.

The cationic polymers hereof can also comprise mixtures of monomer units derived from amine and/or quaternary ammonium-substituted oxyalkylene, vinyl, or other polymerizable monomer and compatible spacer monomers.

The charge density, i.e., the meq/gram of cationic charge, can be controlled and adjusted in accordance with techniques will known in the art. In general, adjustment of the proportions of amine or quaternary ammonium moieties in the polymer, as well as pH of the shampoo composition in the case of the amines, will affect the charge density.

Specific examples of suitable cationic hair conditioning polymers include, for example, copolymers of 1-vinyl-2-pyrrolidone and 1-vinyl-3-methylimidazolium salt (e.g., chloride salt) (referred to in the industry as Polyquaternium-16), such as those commercially available from BASF Wyandotte Corp. (Parsippany, N.J., USA) under LUVIQUAT tradename (e.g., LUVIQUAT FC 370) and copolymers of 1-vinyl-2-pyrrolidone and dimethylaminoethyl methacrylate (referred to in the industry as Polyquaternium-11) such as those commercially available for the Gaf Corporation (Wayne, N.J., USA) under the GAFQUAT tradename (e.g., GAFQUAT 755N).

If included in the shampoos of the present invention, the cationic material should not unduly interfere with the in-use performance and end-benefits of the shampoo, particularly it should not seriously interfere with any anionic surfactants. Generally, if utilized, cationic detersive surfactant will be present at a level of from about 0.05% to about 5%.

The pH of the present compositions is not generally critical and may be in the range of from 2 to about 10, preferably from about 3 to about 9, more preferably from about 4 to about 8.

METHOD OF MANUFACTURE

The compositions of the present invention, in general, can be made by mixing the materials together at elevated temperature, e.g., about 72° C. The silicone resin and silicone fluid component are first mixed together before being mixed with the other ingredients. The complete mixture is mixed thoroughly at the elevated temperature and is then pumped through a high shear mill and then through a heat exchanger to cool it to ambient temperature. The average particle size of the silicone is preferably from about 0.5 to about 20 microns. Alternately, the silicone conditioning agent can be mixed with anionic surfactant and fatty alcohol, such as cetyl and stearyl alcohols, at elevated temperature, to form a premix containing dispersed silicone. The premix can then be added to and mixed with the remaining materials of the shampoo, pumped through a high shear mill, and cooled.

METHOD OF USE

The present compositions are used in a conventional manner for cleaning hair. An effective amount of the composition for conditioning hair in the case of the hair conditioning composition hereof and, in the case of shampoos, an effective amount for cleaning and conditioning hair, typically, from about 1 g to about 20 g of the composition, is applied to hair that has preferably been wetted, generally with water, and then rinsed out. Application to the hair typically includes working the composition through the hair such that most or all of the hair is contacted with the composition. Hair rinses, not containing detersive surfactant, are generally applied to rinsed wet hair after shampooing, and then also rinsed out.

EXAMPLES

The following Examples further describe and demonstrate the preferred embodiments within the scope of the present invention. The Examples are given solely for the purpose of illustration and are not to be construed as limitations of the present invention as many variations thereof are possible without departing from its spirit and scope. All levels given reflect the active weight of the lister material unless otherwise specifically indicated.

Examples 1–6

The following examples exemplify shampoo and hair rinse compositions of the present invention.

| Component | Example # (Wt. %) | | | | | |
|---|---|---|---|---|---|---|
| | 1 | 2 | 3 | 4 | 5 | 6 |
| Ammonium Lauryl Sulfate | 13.50 | 8.50 | 8.50 | 13.50 | | 13.50 |
| Ammonium Laureth Sulfate | 4.00 | 8.50 | 8.50 | 4.00 | | 4.00 |
| Ammonium Xylene Sulfonate | 1.40 | .60 | 1.50 | 1.40 | | 1.40 |
| Ethylene Glycol Distearate | 2.00 | 2.00 | 2.00 | 2.00 | | 2.00 |
| Cocomonoethanol Amide | 1.00 | 1.50 | 1.50 | 1.00 | 1.00 | 1.00 |
| Cetyl Alcohol | .42 | .38 | .42 | .42 | 1.00 | .42 |
| Stearyl Alcohol | .18 | .16 | .18 | .18 | .50 | .18 |
| Tricetyl Methyl Ammonium Chloride | .50 | .50 | .50 | | | .50 |
| Ditallow Dimethyl Ammonium Chloride | | | | | 1.00 | |
| Methyl bis-hydrogenated Tallow Amido Ethyl 2-Hydroxyethyl Ammonium Methyl Sulfate[1] | | | 2.00 | | | |
| LUVIQUAT FC 370[2] | | | | | | .50 |
| Silicone Fluid Component[3] | 2.85 | 1.38 | 1.42 | 2.85 | 1.38 | 2.85 |
| MQ Silicone Resin/Volatile Cyclomethicone[4] | .15 | .12 | .08 | .15 | .12 | .12 |
| Coloring Agent | .64 | .64 | .64 | .64 | .64 | .64 |
| Perfume | 1.20 | 1.00 | 1.00 | 1.20 | 1.20 | 1.20 |
| Preservative | .03 | .03 | .03 | .03 | .03 | .03 |
| Water and Miscellaneous | | | to 100% | | | |

[1]VARISOFT 110 ®, available from Sherex Chemical Company (Dublin, Ohio USA).
[2]LUVIQUAT ® FC 370, a copolymer of vinyl pyrrolidone and methyl vinyl imidazolium chloride available from BASF Wyandotte Corp. (Parsippany, NJ, USA).
[3]A 60:40 wt. ratio blend of polydimethylsiloxane fluid (about 350 centistokes) and polydimethylsiloxane gum (GE SE76, available from General Electric Co., Silicone Products Division (Waterford, NY). centipoise).
[4]A 60:40 wt. ratio blend of the MQ resin in volatile silicone carrier. M:Q molar ratio of about 0.8:1.0.

These compositions can be made by preparing a premix of the entire amount of silicone conditioning agent (i.e., the silicone fluid component and the silicone resin) to be incorporated into the shampoo, along with sufficient ammonium laureth sulfate and cetyl and stearyl alcohol such that the premix comprises about 30% silicone conditioning agent, about 69% surfactant, and about 1% of the alcohols. The premix ingredients are heated and stirred at 72° C. for about 10 minutes and the premix is then conventionally mixed with the remaining hot ingredients. The composition is then pumped through a high shear mixer and cooled.

The hair rinse conditioner of Example 5 is made by mixing the ingredients together at about 72° C. for about 10 minutes.

The compositions of Examples 1–4 and 6 can provide excellent in-use hair cleaning and conditioning, along with high silicone hair conditioning agent efficiency. The composition of Example 5 can provide excellent hair conditioning along with high silicone hair conditioner efficiency.

What is claimed is:

1. A hair conditioning shampoo composition comprising:
   (a) from about 5% to about 50% of a detersive surfactant component;
   (b) from about 0.1% to about 10%, by weight, of a dispersed silicone hair conditioning component, said hair conditioning component having a viscosity of up to about 2,000,000 centistokes at 25° C. and comprising:
      (i) a nonvolatile, insoluble, silicone fluid component; and
      (ii) silicone resin, said silicone resin being soluble in said silicone polymer fluid component and insoluble in water and in said shampoo composition and selected from the group consisting of MO resins, MT resins, MDT resins, MDO resins, MTO resins, and MDTO resins, and mixtures thereof, said resin component having at least about 1.1 oxygen atoms per silicone atom and being free of silane linkages; wherein the weight ratio of (i):(ii) is from about 9:1 to about 200:1; and
   (c) an aqueous carrier.

2. A shampoo composition as in claim 1, further comprising a silicone hair conditioning component suspending agent.

3. A shampoo composition as in claim 2, wherein said composition is in the form of a pourable liquid.

4. A shampoo composition as in claim 1, wherein said silicone resin component comprises MQ resin.

5. A shampoo composition as in claim 4, wherein said MQ resin has an M:Q ratio of from about 0.5:1.0 to about 1.5:1.0.

6. A shampoo composition as in claim 2, wherein said silicone fluid component comprises a mixture of polydimethylsiloxane gum having a viscosity greater than about 1,000,000 centipoise and polydimethylsiloxane fluid having a viscosity of from about 10 centipoise to about 100,000 centipoise, said mixture having a gum:fluid weight ratio of from about 30:70 to about 70:30.

7. A shampoo composition as in claim 1, wherein said non-volatile, silicone fluid component comprises a mixture of polydimethylsiloxane gum having a viscosity greater than about 1,000,000 centipoise and dimethicone fluid having a viscosity of from about 10 centipoise to about 100,000 centipoise, said mixture having a gum:fluid weight ratio of from about 30:70 to about 70:30.

8. The shampoo composition of claim 2 wherein the detersive surfactant is selected from anionic, nonionic, zwitterionic, and amphoteric surfactants, and mixtures thereof.

9. The shampoo composition of claim 8 wherein the detersive surfactant comprises one or more anionic surfactants.

10. The shampoo composition of claim 9 wherein the detersive surfactant is at a level of from about 10% to about 30% by weight of the composition.

11. The shampoo composition of claim 11 wherein the surfactant comprises alkyl sulfates, ethoxylated alkyl sulfates, or mixtures thereof.

12. The shampoo composition of claim 11 wherein the surfactant is selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine luaryl sulfate, diethanolamine laureth sulfate, lauric monoglyceride sodium sulfate, sodium lauryl sulfate, sodium laureth sulfate, potassium lauryl sulfate, potassium laureth sulfate, aluryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauroyl sulfate, triethanolamine lauroyl sulfate, triethanolamine lauroyl sulfate, sodium tridecyl benzene sulfonate, sodium dodecyl benzene sulfonate, and mixtures thereof.

13. A shampoo composition as in claim 8 further comprising from about 0.1% to about 5%, by weight, of a cationic conditioning agent.

14. A hair conditioning composition comprising:
  (a) from about 0.1% to about 10%, by weight, of a dispersed silicone hair conditioning component, said hair conditioning component having a viscosity of up to about 2,000,000 centistokes at 25° C. and comprising:
    (i) a nonvolatile, insoluble, silicone fluid component; and
    (ii) silicone resin, said silicone resin being soluble in said silicone fluid component and insoluble in water and in said composition and selected from the group consisting of resins, MT resins, MDT resins, MDO resins, MTO resins, and MDTO resins, and mixtures thereof, said resin component having at least about 1.1 oxygen atoms per silicone atom and being free of silane linkages;
  wherein the weight ratio of (i):(ii) is from about 9:1 to about 200:1; and
  (b) an aqueous carrier.

15. A hair conditioning composition as in claim 14, further comprising a silicone hair conditioning component suspending agent.

16. A hair conditioning composition as in claim 15, wherein said composition is in the form of a pourable liquid.

17. A shampoo composition as in claim 14, wherein said silicone resin component comprises MQ resin.

18. A hair conditioning composition as in claim 17, wherein said MQ resin has an M:Q ratio of from about 0.5:1.0 to about 1.5:1.0.

19. A hair conditioning composition as in claim 15, wherein said silicone fluid component comprises a mixture of polydimethylsiloxane gum having a viscosity greater than about 1,000,000 centipoise and polydimethylsiloxane fluid having a viscosity of from about 10 centipoise to about 100,000 centipoise, said mixture having a gum:fluid weight ratio of from about 30:70 to about 70:30.

20. A hair conditioning composition as in claim 18, wherein said nonvolatile, silicone fluid component comprises a mixture of polydimethylsiloxane gum having a viscosity greater than about 1,000,000 centipoise and dimethicone fluid having a viscosity of from about 10 centipoise to about 100,000 centipoise, said mixture having a gum:fluid weight ratio of from about 30:70 to about 70:30.

21. A hair conditioning composition as in claim 15 further comprising from about 0.1% to about 5%, by weight, of a cationic conditioning agent.

22. A hair conditioning composition as in claim 21, wherein said cationic conditioning agent is selected from the group consisting of ditallow dimethyl ammonium chloride, stearyl dimethyl benzyl ammonium, stearyl trimethyl ammonium chloride, tricetyl methyl ammonium chloride.

23. A method for cleaning and conditioning hair comprising applying an effective amount of the shampoo of claim 1 to the hair and then rinsing said composition from the hair.

24. A method for cleaning and conditioning hair comprising applying an effective amount of the composition of claim 2 to the hair and then rinsing said composition from the hair.

25. A method for conditioning the hair comprising applying the composition of claim 14 to the hair and then rinsing said composition from the hair.

26. A method for conditioning the hair comprising applying the composition of claim 14 to rinsed, wet hair subsequent to shampooing, and then rinsing said composition from the hair.

27. A hair conditioning shampoo according to claim 1, wherein the ratio of (i) :(ii) is from about 9:1 to about 100:1.

28. A hair conditioning composition according to claim 14, wherein the weight ratio of (i):(ii) if from about 9:1 to about 100:1.

* * * * *